United States Patent [19]
Samarasekera et al.

[11] Patent Number: 5,970,111
[45] Date of Patent: Oct. 19, 1999

[54] FAST AND EFFICIENT MULTIPROCESSOR IMPLEMENTATION FOR EXACT FOR AN EXACT CONE BEAM IMAGE RECONSTRUCTION

[75] Inventors: Supun Samarasekera; Frank Sauer, both of Princeton; Kwok Tam, Edison; Ali R. Bani-Hashemi, Belle Mead, all of N.J.

[73] Assignee: Siemens Corporate Research, Inc., Princeton, N.J.

[21] Appl. No.: 09/109,266

[22] Filed: Jun. 30, 1998

Related U.S. Application Data

[63] Continuation-in-part of application No. 08/940,489, Sep. 30, 1997, Pat. No. 5,901,196.

[51] Int. Cl.[6] ....................................................... A61B 6/03
[52] U.S. Cl. ............................................... 378/4; 378/901
[58] Field of Search ......................... 378/4, 901; 382/131

[56] References Cited

U.S. PATENT DOCUMENTS

| | | | |
|---|---|---|---|
| 5,333,164 | 7/1994 | Tam | 378/8 |
| 5,500,883 | 3/1996 | Hsiao et al. | 378/4 |
| 5,559,846 | 9/1996 | Tam | 378/4 |
| 5,566,341 | 10/1996 | Roberson et al. | 395/800 |
| 5,862,198 | 1/1999 | Samarasekera et al. | 378/4 |

*Primary Examiner*—David Vernon Bruce
*Attorney, Agent, or Firm*—Lawrence C. Edelman

[57] ABSTRACT

A computed tomographic imaging apparatus performs three-dimensional (3D) image reconstruction of a region of interest of an object using a plurality of processors for processing successive sets of cone beam measurement data that are acquired by scanning about the object with a cone beam radiation source and an area detector. A central memory has stored therein a plurality of subsets of pre-calculated image processing information, and the plurality of processors are responsive to a given sequence of successive ones of the subsets of pre-calculated image processing information for converting the cone beam measurement data to Radon derivative data on a plurality of Radon $\phi$-planes. In a preferred embodiment each of the processors has a first input coupled for receiving in a broadcast manner the successive sets of cone beam measurement data, and a second input coupled for receiving the subsets of pre-calculated image processing information in a given sequence so that each one of the plurality of processors converts the cone beam measurement data broadcast to its second input into Radon derivative data for a respective subset of the Radon $\phi$-planes.

7 Claims, 7 Drawing Sheets

FAST AND EFFICIENT MULTIPROCESSOR IMPLEMENTATION FOR EXACT FOR AN EXACT CONE BEAM IMAGE RECONSTRUCTION

CROSS-REFERENCE TO RELATED APPLICATIONS

"This is a continuation-in-part of application Ser. No. 08/940,489, filed Sep. 30, 1997 now U.S. Pat. No. 5,901,196."

BACKGROUND OF THE INVENTION

1. Field of the Invention

The present invention relates generally to computed tomographic (CT) imaging apparatus that performs three-dimensional (3D) image reconstruction by processing cone beam measurement data representative of an object, and more specifically, to a fast and efficient multiprocessor arrangement for performing the image reconstruction processing.

2. Description of the Background Art

Recently a system employing cone beam geometry has been developed for three-dimensional (3D) computed tomographic (CT) imaging that includes a cone beam x-ray source and a 2D area detector. An object to be imaged is scanned, preferably over a 360° angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sets of cone beam projected measurement data (referred to hereinafter as measurement data), each set of measurement data being representative of x-ray attenuation caused by the object at a respective one of the source positions. After completion of measurement data acquisition, the measurement data is processed for reconstructing a 3D image of the object.

As compared with the processing required for reconstructing an image when using an x-ray source supplying parallel or fan beams, the processing of the measurement data acquired when using a cone beam source is computationally much more complex. This is because when using a parallel or fan beam source, the measurement data is already directly representative of a 2D Radon transform of a cross-section of the object. However, this is not the case when using a cone beam source, and complex processing of the acquired measurement data is required to develop appropriate Radon transform data. Such processing for exactly reconstructing an image of the object typically, comprises:

1) conversion of the measurement data to Radon derivative data. This may be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference, 2) conversion of the Radon derivative data to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference, and 3) performing an inverse 3D Radon transformation of the Radon data using known techniques, such as those described in detail in the forenoted U.S. Pat. No. 5,257,183 for reconstructing image data that, when applied to a display, provides a view of the 3D CT image of the object.

Although the theory for exactly reconstructing an image using cone beam measurement data is generally known, such as from the US patents noted above, a practical implementation of the processing turns out to be quite problematic. Not only is the amount of measurement data to be processed very large and rapidly acquired in accordance with a timing that is mainly determined by the geometry of the scan path, but, as noted above, the calculations required on the acquired data are quite complex. The most computationally expensive part of the object reconstruction is the calculation of the Radon derivative data (steps 1 and 2 noted above). As noted in the above US patents, as well as in detail in U.S. Pat. No. 5,463,666 entitled HELICAL AND CIRCLE SCAN REGION OF INTEREST COMPUTERIZED TOMOGRAPHY issued Oct. 31, 1995, hereby incorporated by reference, for calculating the value of the Radon data at a given Radon sample point, it is typically necessary to process the measurement data acquired from several source positions, with the measurement data from each source position developing a contribution to the final value for that sample point by way of data combination. Typically one needs to calculate about $100 \times 10^6$ line integral derivatives during object reconstruction. Since each line integral derivative requires the calculation of two single line integrals (because one uses the difference between two closely spaced line integrals to calculate a single line integral derivative) $200 \times 10^6$ single line integral calculations are required. However, before one can even begin to perform these line integral derivative calculations, one has to compute for each Radon sample which source positions will provide the measurement data that must be processed, and determine the extent of the lines on the measurement data along which the integration must be performed. In order to compute the contributing source positions, one has to intersect the source scanning path with the Radon integration plane as explained in the forenoted U.S. Pat. No. 5,463,666. When using a spiral scan path, this requires the solution of transcendental equations, which are computationally expensive. The complexity of these above-noted calculations leads to severe bottlenecks in processing of the measurement data, so as to prevent rapid and efficient image reconstruction.

U.S. patent application Ser. No. 08/940,489, entitled A REDUCTION OF HITLIST SIZE IN SPIRAL CONE BEAM CT BY USE OF LOCAL RADON ORIGINS, filed Sep. 30, 1997, incorporated herein by reference, describes a rapid and efficient technique for processing the acquired measurement data to develop the Radon derivative data. A spherical coordinate system (r, θ, φ) defining a Radon space partitioned by a plurality of vertically oriented co-axial φ-planes is used to facilitate a subsequent inversion processing of the Radon data. Instead of performing all of the conversion calculations "on the fly", this new technique makes use of a pre-calculated "relative hitlist" for speeding up the conversion.

Briefly, the relative hitlist comprises a memory of pre-calculated image reconstruction processing information which is used to greatly aid the conversion of the measurement data to Radon data. The hitlist information is determined primarily by geometric parameters of the imaging apparatus, and are therefor already determined before imaging operation of the apparatus. Such parameters are the pitch and other characteristics of the source/detector scan path, the dimensions of the object, the detector resolution, and the sampling of the scan path and the Radon space. These parameters define the line integrals which need to be calculated in the measurement data to develop the desired samples of the Radon data. Thus, the hitlist information indicates the correspondence between points in Radon space and the source positions that contribute thereto, parameters that define the line integrals that need to be calculated in the measurement data acquired at each of the source positions, as well as other information useful for image reconstruction processing. Typically the imaging system manufacturer will pre-calculate the hitlist information and store it in a memory. The hitlist information is used during run-time (imaging) operation of the apparatus to assist the conversion processing of the acquired measurement data into the many samples of Radon derivative data needed to fill up the region of Radon support for proper reconstruction of the object. Furthermore, due to a symmetry that is induced in the subsequent Radon inversion processing, the information that is stored for only one of the Radon space $\phi$-planes can be used for calculating Radon derivative data for all of the other Radon space $\phi$-planes. Accordingly, the memory requirements for the hitlist are greatly reduced. Use of the pre-calculated hitlist results in a great improvement in the speed and efficiency of the image reconstruction processing as compared to conversion processing without use of a hitlist.

It would be desirable to provide an efficient multiprocessor arrangement for carrying out image reconstruction processing which uses such pre-calculated information.

SUMMARY OF THE INVENTION

In accordance with the principles of the present invention, a computed tomographic imaging apparatus performs three-dimensional (3D) image reconstruction of a region of interest of an object using a plurality of processors for processing successive sets of cone beam measurement data that are acquired by scanning about the object with a cone beam radiation source and an area detector. A central memory has stored therein a plurality of subsets of pre-calculated image processing information, and the plurality of processors are responsive to successive ones of the subsets of pre-calculated image processing information for converting the cone beam measurement data to Radon derivative data on a plurality of Radon $\phi$-planes. Each of the processors has a first input coupled for receiving in a broadcast manner the successive sets of cone beam measurement data, and a second input coupled for receiving the subsets of pre-calculated image processing information in a given sequence so that each one of the plurality of processors converts the cone beam measurement data broadcast to its second input into Radon derivative data for a respective subset of said Radon $\phi$-planes. In one preferred embodiment of the invention, a plurality of local memories coupled to one another for transferring the subsets of pre-calculated image processing information therebetween in a pipeline manner, are also coupled to the second input of respective ones of said plurality of processors.

DETAILED DESCRIPTION OF THE PREFERRED EMBODIMENTS

Figure 1:
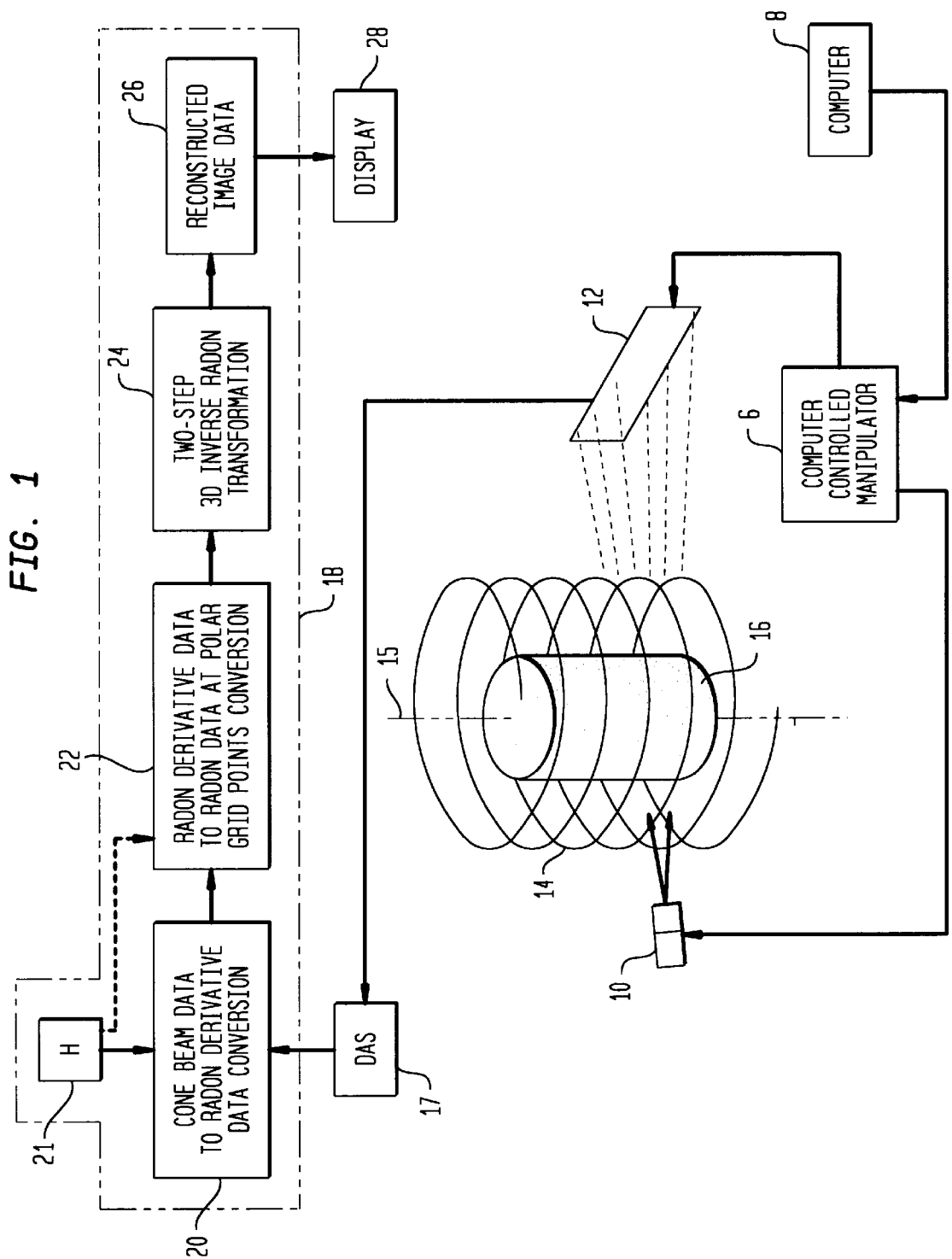
FIG. 1 is a block diagram and simplified perspective illustration of the imaging of an object using a cone beam imaging apparatus, wherein a hitlist of pre-calculated information is used for image reconstruction processing.

FIG. 1 illustrates a cone beam 3D CT imaging apparatus that operates in accordance with the principles of the present invention. Except as to be specifically described later with respect to implementation of image reconstruction processing in accordance with the present invention, the illustrated imaging apparatus is constructed and operates substantially the same as described in the forenoted U.S. Pat. Nos. 5,257,183 and 5,446,776.

Briefly, referring again to FIG. 1, a computer controlled manipulator 6, in response to control signals from an appropriately programmed computer 8, cause a source 10 of cone beam energy (such as x-rays) and a two-dimensional array detector 12 to cooperate (scan) at a plurality of discrete, sequentially occurring, adjacent source positions, along a pre-defined source scanning path, illustrated as a spiral scan path 14 centered on a predetermined axis 15 of an object 16. As a result of the source/detector cooperation, detector 12 acquires complete cone beam measurement data which is then used for reconstructing an image of object 16. Alternatively, and equivalently, object 16 could be rotated and translated to cause scanning by a fixed position source and detector. Furthermore, the scanning can be accomplished in a continuous or stepwise manner, and the spiral path can have equally spaced turns (sometimes referred to as stages), or turns with decreasing pitch at the top and bottom edges of a region of interest of the object. Even furthermore, although source 10 is shown as an x-ray source, other types of imaging energy might be useful, such as neutrons, positrons, etc.

Computer 6, manipulator 8, source 10 and detector 12 cooperate to accomplish scanning of the object in a manner generally well understood by those skilled in this art, i.e., such as described in detail in the forenoted U.S. Pat. No. 5,463,666, and therefore discussion of further details of this portion of the operation of the cone beam imaging apparatus is deemed not necessary.

After the x-ray energy passes through the field of view of the imaging apparatus, measurement signals corresponding to the sensed x-ray energy falling on elements within detector 12 are supplied to a data acquisition system (DAS) 17 which, like the previously described portions of FIG. 1, may operate in a fashion well known to those of ordinary skill in this technology for digitizing, pre-processing, and storing of measurement data corresponding to the acquired measurement signals.

The measurement data from DAS 17 is supplied to a buffer memory and image reconstruction processor 18, which generally comprises a computer programmed to perform various data conversions that process the measurement data so as to reconstruct an image, the functionality of the processing being illustrated by blocks 20 to 26 within processor 18. More specifically, at block 20 the measurement data is processed so as to be converted to Radon derivative data. A spherical coordinate system (r, θ, φ) is preferably used to facilitate the Radon inversion processing. As will be described in greater detail later, this is accomplished by use of a "relative" hitlist ($H_r$) of pre-calculated image reconstruction processing information that is stored in a database 21, and used during run-time (imaging) operation of the apparatus for processing the acquired measurement data to develop Radon derivative data.

Figure 5:
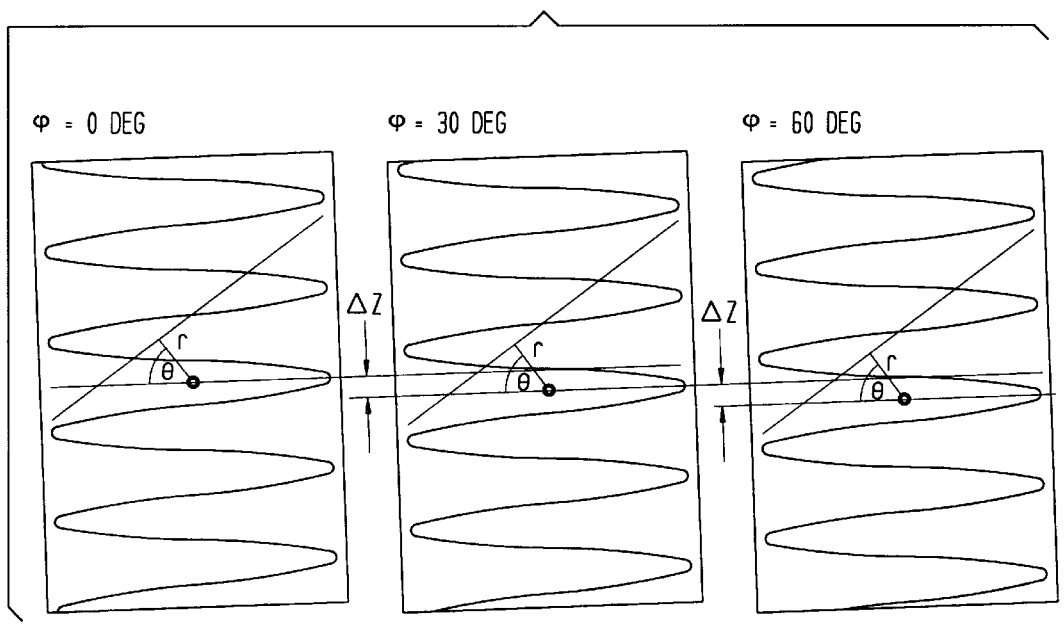
FIG. 5 illustrates use of the technique of local Radon origins for successive $\phi$-planes of FIG. 4, for inducing a symmetry into the determinations illustrated therein and enabling the use of a relative hitlist having reduced size.

At block 22 the Radon derivative data is converted to Radon data at equally spaced polar grid points using, for example, the technique described in detail in conjunction with FIG. 5 of the forenoted U.S. Pat. No. 5,446,776. Briefly, as described therein, the Radon derivative data from block 20 is converted to Radon derivative data at equally spaced polar grid points using nearest neighbor or interpolation techniques, and then summed to develop the Radon data at equally spaced polar grid points. The hitlist of reconstruction processing information stored in database 21 preferably also provides pre-calculated information during this portion of the reconstruction processing, such as weighting information used for interpolation processing (as indicated by a dashed line from block 21 to block 22), thereby also improving the speed and efficiency of this portion of the reconstruction processing.

Figure 2:
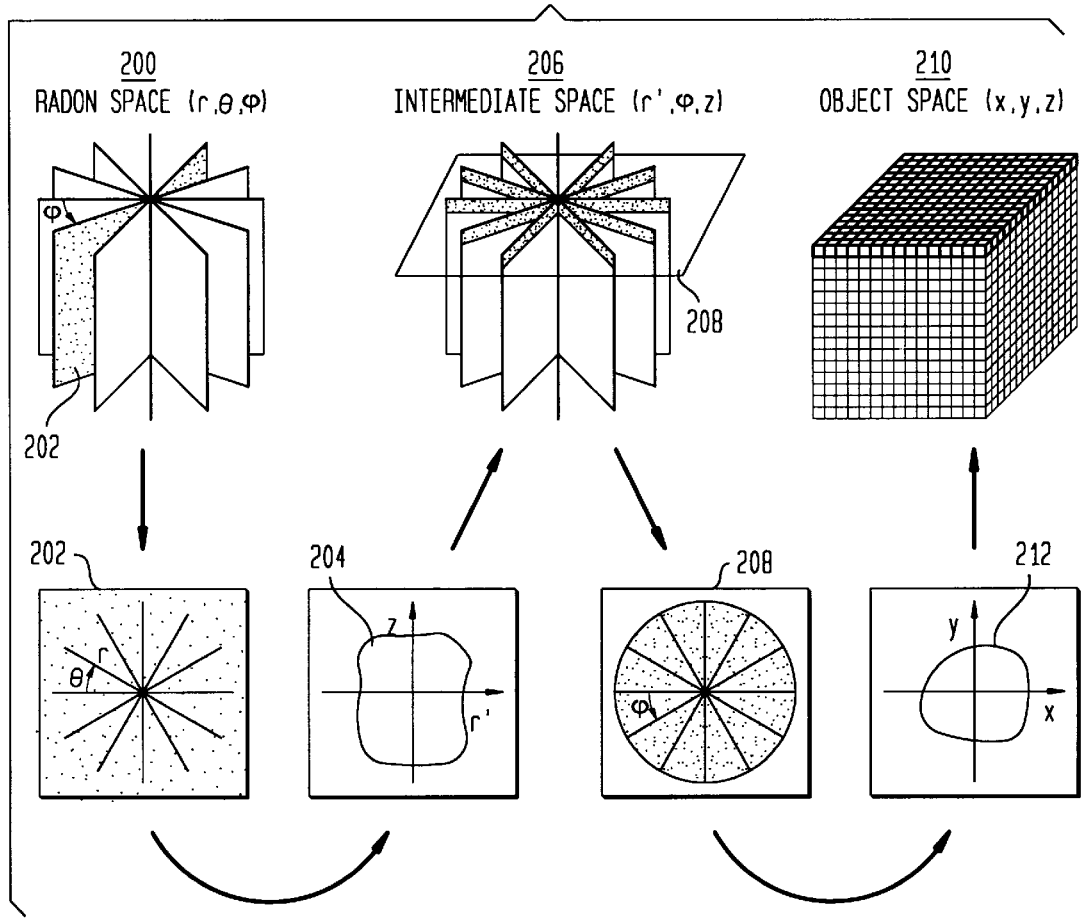
FIG. 2 illustrates inverse 3D Radon transformation processing.

At block 24 the Radon data is subjected to inverse 3D Radon transformation processing. FIG. 2 generally illustrates one example of a two-step 3D Radon inversion procedure which is used in conjunction with the present invention. The two-step 3D Radon inversion processing of block 24, except for a slight modification which will be described later, is known and described, for example, in the forenoted U.S. Pat. No. 5,257,183. Briefly, one starts with the Radon data from block 22, sampled in a Radon space 200 that is defined by a spherical coordinate system (r, θ, φ), with one φ-plane 202 of a plurality of vertically oriented coaxial φ-planes being illustrated with a polar grid coordinate thereon. In the first inversion processing step, 2-D Radon inversions are performed on the Radon data in each of the φ-planes using a procedure such as filtered backprojection. Each φ-plane 202 will then contain a 2-D projection 204 of the object for the corresponding viewing angle, sampled in a Cartesian coordinate system (r',z). After completion of the first 2D inversion, information about the whole object is contained in a cylindrical coordinate space 206 (r',φ,z). In the second inversion step, horizontal planes (z-slices) 208 parallel with the z axis are defined in space 206 and data in those planes are subjected to inversion processing to develop data descriptive of a 3D image of the object in object space 210, slice-by-slice. More specifically, for each z-slice 208, a 2D CT reconstruction procedure, such as filtered backprojection, operates on the values of the 2D projection images in the plane of the z-slice, thereby calculating a 2D image 212 of the object for each z-slice. The final result is image data representative of the spatial distribution of the 3D object, sampled in the Cartesian coordinate system (x,y,z).

Referring back to FIG. 1, the image data developed by block 24 is stored at block 26, and then fed from reconstruction processor 18 to a display 28, which may operate in known fashion, to provide a 3D CT view of object 16.

Except for the determination and use of the relative hitlist, which is described next, a more detailed description of the blocks of FIG. 1 can be found in the forenoted U.S. patents.

As previously noted, and as described in detail in the forenoted U.S. patent application Ser. No. 08/940,489, before operation of a cone beam imaging apparatus for acquiring and processing of measurement data to reconstruct an image of an object, information required for processing of the acquired measurement data is pre-calculated and stored in database 21, alternatively referred to as a hitlist. The pre-calculated information is then used during the imaging operation of the cone beam apparatus for processing of the acquired measurement data to develop the Radon derivative data. In general, the hitlist contains processing information that is determined primarily by geometric parameters of the imaging apparatus that are predetermined during its imaging operation, such as the pitch and other parameters of the source/detector scan path, the dimensions of the object, the detector resolution, and a desired sampling of the scan path and the Radon space. The hitlist information indicates the correspondence between points in Radon space and the source positions that contribute thereto, parameters that define the line integrals that need to be calculated in the measurement data acquired at each of the source positions, as well as other information useful for image reconstruction processing.

Pre-calculation of the hitlist information provides a very significant speed-up of the run-time (image) processing of the measurement data and results in a greatly improved efficiency in the implementation of the image reconstruction processing. However, as described in more detail in the forenoted U.S. patent application Ser. No. 08/940,489, since hitlist information is required for determining data for each of the many points in Radon space that define the objects region of support, the size of the hitlist is actually quite large.

Consequently, to reduce the size of the hitlist, a symmetry is induced into the image reconstruction processing that determines the correspondence between points in Radon space and the source positions. As a result of such induced symmetry, hitlist information calculated for determining contributions to the Radon points of one of the φ-planes is also appropriate for processing measurement data to develop contributions to the Radon data for other ones of the φ-planes. The manner of inducing this symmetry in the image reconstruction processing will be described in conjunction with FIG. 5.

Figure 3A:
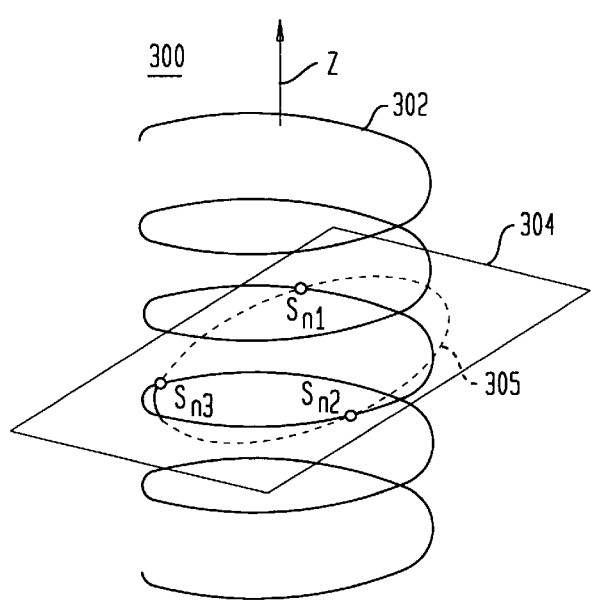
FIGS. 3a and 3b illustrate determination of the source positions which contribute to a given Radon sample point.
Figure 3B:
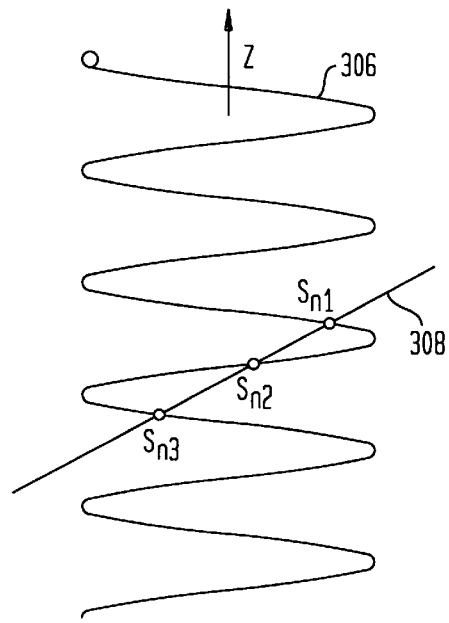
Figure 4:
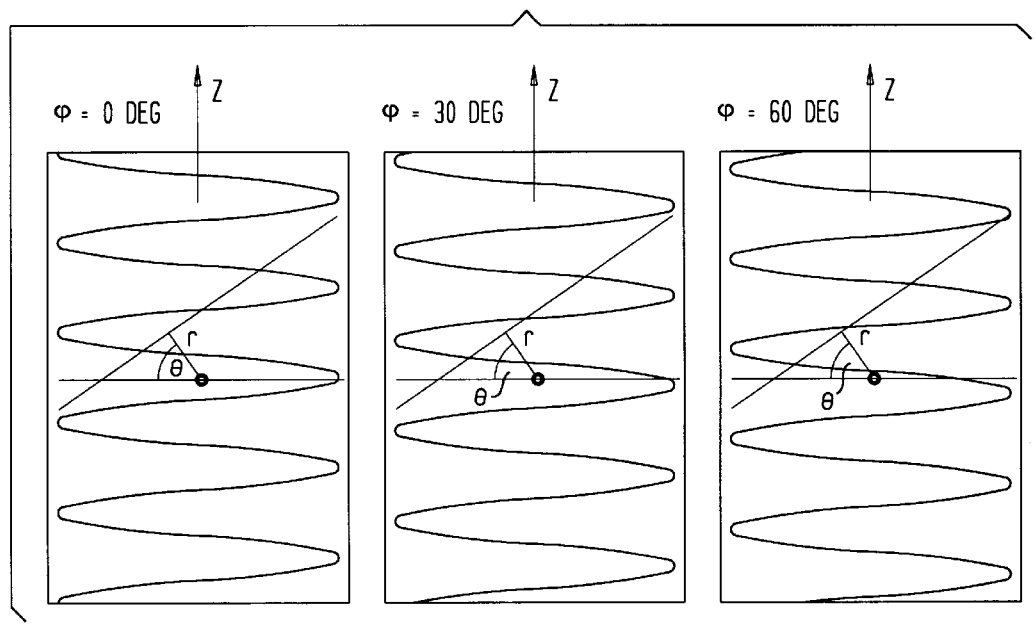
FIG. 4 illustrates determination of the source positions which contribute to a Radon sample point which is similarly positioned on selected ones of successive $\phi$-planes in Radon space.

However, before describing in detail how the symmetry is induced, the reader is referred to FIGS. 3 and 4 for some additional background information. FIG. 3 illustrates determination of the source positions $S_{n1}$, $S_{n2}$ and $S_{n3}$ along scan path 302 which acquire measurement data to be processed for contributing to a given Radon sample point. As well known by those skilled in this art, 3D Radon transform datum at a given point (r, θ, φ) can be uniquely determined by the planar integral of the object's x-ray attenuation coefficient, with the integration plane determined by the vector (r, θ, φ), not specifically shown. The measurement data acquired by the detector at source positions which lie on the integration plane contribute to the particular Radon value. FIG. 3a depicts this situation in 3D. The illustrated exemplary integration plane 304 intersects the spiral scan path 302 at positions $S_{n1}$, $S_{n2}$ and $S_{n3}$. The intersections lie on an ellipse, shown by dashed line 305, which is generated by projecting the spiral in the z-axis direction onto integration plane 304. To calculate the source intersections, one merely projects both scan path 302 and integration plan 304 into the φ-plane (determined by the φ-coordinate of the Radon point), as shown in FIG. 3b. Then, one merely has to solve the 2-D problem of intersecting a sine-function 306 (projection of spiral 302 into the φ-plane) with a line 308 (projection of plane 304 into the φ-plane) to determine the position of points $S_{n1}$, $S_{n2}$ and $S_{n3}$. Finally, one translates these positions back into 3D space based on knowledge of the geometry of scan path 302. This procedure is repeated until source position information is developed for all the Radon points that are desired for reconstructing an image of the object with a desired resolution.

FIG. 4 illustrates determination of the source positions which contribute to Radon sample points which are similarly positioned on selected ones of successive φ-planes in Radon space, i.e., Radon sample points which have the same r and θ coordinates, with exemplary φ-planes 0°, 30° and 60° being illustrated. As shown thereby, as one moves from φ-plane to φ-plane while keeping r and θ constant, the spiral's projection shifts along the z-axis, which results in new intersections. Unfortunately, the new intersections are related to the previous ones in a highly nonlinear way. When one stores these results in the hitlist, one needs separate, i.e., unique, entries for the Radon sample points of each of the many φ-planes partitioning the Radon space. For a more detailed description, the reader is referred to the forenoted U.S. Pat. No. 5,257,183 (FIGS. 3–10), or the forenoted U.S. patent application Ser. No. 08/940,489.

Although the position of the intersections of projections of the integration planes with the spiral scan path (i.e., contributing source positions) changes between the φ-planes in a highly nonlinear way, the shift of the spiral's projection along the z-axis changes in a very predictable, and in fact linear way. As shown by the three φ-planes illustrated in FIG. 4, the projection of the spiral scan path "shifts" in the z-axis direction with increases in the φ-plane index (e.g., from 0° to 30° to 60°). The technique of the relative hitlist takes advantage of this predictability in that the hitlist entries calculated for the Radon sample points on one φ-plane can be used for the similarly positioned Radon sample points in other ones, and in fact all of the other ones, of the φ-planes. A visual illustration of the technique used to achieve this result is shown in FIG. 5. As shown therein, the Radon origin on each of successive ones of the φ-planes (with only φ-planes 0°, 30° and 60° being illustrated) is shifted by an amount (Δz) corresponding to the amount of z-axis shift that the projection of the spiral path 302 experiences between the successive φ-planes. The ΔZ illustrated in FIG. 4 corresponds to Δz times the number of φ-planes between 0° and 30°.

As a result of the origin shift for successive φ-planes, the intersections between the projections of the spiral and the integration plane are the same in the local coordinate systems of each φ-plane. Consequently, the same source positions, in a relative sense, contribute to a given r,θ Radon position independent of the φ-plane, and the reconstruction information in the hitlist intended for a given φ-plane can now be re-used for determining Radon data in any of the successive φ-planes. All that remains to be done is to make a compensation in the processing that follows to take into account the φ-plane origin shifts.

Accordingly, the two-step Radon inversion processing of block 24 of FIG. 1, allows one to establish on each of the φ-planes containing the Radon transform data, a local Radon origin, which local origin is independent of the local origin of each of the other ones of the φ-planes. Thus, the shifting of the local Radon origins of the Radon space φ-planes can be kept track of, and compensated for during Radon inversion processing.

More specifically, the compensation can be made during the first step of the Radon inversion processing shown in FIG. 2, by backprojecting the Radon data (from φ-planes) onto sample grids (z,r') which are not shifted, i.e., are offset, from the local Radon origins. Thus, the sample grids are already aligned in the z-axis direction and as such are part of a global grid. Consequently, the z-axis offset of the Radon origins is simply taken into account by introducing a corresponding z-axis delta into the coordinate variables during the Radon inversion backprojection. Alternatively, one can backproject onto z,r' grids which are shifted along with the local Radon origins, and then, before one performs the second step of the inversion processing (2D Radon inversion in the φ-planes), shifting the backprojection results, i.e., images 204, a corresponding amount in the z-axis direction to compensate for the previous z-shift. This shifting can easily be accomplished using standard interpolation techniques.

What follows is a description of how to calculate the information included in "relative" hitlist 21, and how to extract information about all the φ-planes from it. First, it is necessary to introduce some nomenclature.

Nomenclature

The spiral scan path is defined in a cylindrical coordinate system, where the z-axis coincides with the axis of the spiral.

The Radon space is defined in regard to a spherical coordinate system for which the axis, around which the angle φ is measured, coincides with the z-axis of the cylindrical coordinate system.

The spiral scan path is sampled in equidistant φ-intervals with step size $\Delta\phi_{source}$. The sampled source positions along the scan path are denoted by $S_n$, n=0 ... $N_s$-1. The number of source positions $N_s$ depends on the length of the scan path and the sampling interval.

The φ-planes in Radon space are sampled in equidistant φ-intervals with step size $\Delta\phi_{Radon}$. The sampled φ-planes are denoted by $\phi_m$, m=0 ... M-1. The number of φ-planes is given by M=π/$\Delta\phi_{Radon}$. The step size $\Delta\phi_{Radon}$ has to be chosen such that M is an integer. It is advantageous to make M an even integer, which we assume to be true in the following. We also make the assignments $\phi_0$=-π/2 and $\phi_{M-1}$=π/2-$\Delta\phi_{Radon}$, which leads to the correspondence $\phi_{M/2}$=0.

For the concept of local Radon origins to work in a straightforward way, we assume that $\Delta\phi_{source}$=$\Delta\phi_{Radon}$.

We use a different Radon origin for each of the different φ-planes. When we move from one φ-plane to the next by the angular distance Δφ=$\Delta\phi_{Radon}$, we translate the local Radon origin by Δz. The shift Δz is determined by the pitch p of the spiral scan path and the angular sampling interval on the scan path Δφ=$\Delta\phi_{source}$. The pitch p of the spiral is defined by how much the spiral path progresses in the z-direction during a full 2π-turn. When we move from one source sample on the spiral to the next by Δφ(=$\Delta\phi_{source}$=$\Delta\phi_{Radon}$), we move in the z-direction by Δz=p.$\Delta\phi_{source}$/2π. Hence, by applying the same shift Δz to the local origins of the φ-planes in Radon space, we can, in regard to the local coordinate systems, make the projection of the spiral scan path look the same on every φ-plane. This enables us to use the information in the relative hitlist for determining Radon data for all the φ-planes.

Details of Hitlist Calculation

In order to calculate the hitlist information, we first select one particular φ-plane in Radon space, which will be used to calculate the information for the relative hitlist. This plane is referred to as the $\phi_{M/2}$-plane. Next, we calculate how each sampled source position $S_n$ contributes to the Radon data in the $\phi_{M/2}$-plane, i.e. to all the sampled Radon positions $(r_i, \theta, \phi_{M/2})$ which lie in this plane. We go through all the sampled Radon positions $(r_i, \theta, \phi_{M/2})$ and calculate for each such Radon position the contributing source positions, as described above in conjunction with FIG. 3.

Ideally, one would like to have measurements taken with the source being located at these exact intersections. However, since the scan path is sampled, one has to choose the actual source positions which come closest to the ideal positions. One can use either a nearest neighbor approach (picking the real source position which is closest to the ideal position) or an approach with interpolation (letting the two real source positions which are closest to the ideal position contribute in a weighted manner).

This Radon space driven hitlist is then re-sorted into the desired source space driven version, where the information is ordered source position by source position. The source driven version of the relative hitlist is stored for use during the image reconstruction processing of acquired measurement data, as previously described.

Details of Hitlist Structure

We refer to the information stored in the relative hitlist as $$I_n \equiv \tilde{I}_{n,M/2}, \; n=0 \ldots N_I$$

The integer $N_I$ may be required to be larger than the number of source positions $N_S$, but it can also be smaller. The exact relationship between $N_I$ and $N_S$ depends on the relative size of the object in regard to parameters of the spiral scan path. $\tilde{I}_{n,M/2}$ means that the particular information is for source position $S_n$ with regard to the $\phi_{M/2}$-plane in Radon space.

$\tilde{I}_{n,M/2}$ may have the following structure, containing a list of Radon positions (on the $\phi_{M/2}$-plane) to which source $S_n$ contributes, and the parameters specifying the corresponding integration lines:

| $I_n \equiv \tilde{I}_{n,M/2} =$ | |
|---|---|
| n, {Radon point #1 , | Line parameters for point #1, |
| (e.g., indices i,j of Radon sample position $r_i, \theta_j$) | (e.g., start and endpoint of an integration line) |
| Radon point #2, | Line parameters for point #2, |
| Radon point #3, | Line parameters for point #3, |
| ..... | ..... } |

For a further understanding of how to use the relative hitlist, consider how the measurement data acquired from source position $S_n$ contribute to the $\phi_m$-planes for $m \neq M/2$. With the local Radon origins shifted as described above, we have the following situation: the coordinates of source position $S_{n-1}$ with respect to the local coordinate system of the $\phi_{M/2}$-plane are the same as those of source position $S_n$ viewed from the local coordinate system of the $\phi_{M/2+1}$-plane. Hence, the measurement data from source position $S_n$ contributes to the Radon positions in the $\phi_{M/2+1}$-plane just like the measurement data from source position $S_{n-1}$ contributes to the Radon positions in the $\phi_{M/2}$-plane. The corresponding information is stored in $I_{n-1}$. This holds true if indices n and m increase in the same direction. If index n increases in the direction in which m decreases, measurement data from source position $S_{n+1}$ contributes to the Radon positions in the $\phi_{M/2}$-plane just like the measurement data from source position $S_n$ contributes to the Radon positions in the $\phi_{M/2+1}$-plane.

In general, if $I_{n,m}$ denotes the image reconstruction information for processing the measurement data from source position $S_n$ for developing contributions to the Radon positions in the $\phi_m$-plane, the following general relationship holds:

$$I_{n,m} = I_{n \pm \Delta m, M/2} \equiv I_{n \pm \Delta m} \text{ with } \Delta m = M/2 - m$$

i.e. we find the information $I_{n,m}$ in the relative hitlist by looking up how source $S_{n \pm \Delta m}$ contributes to the $\phi_{M/2}$-plane. Again, the plus sign applies if indices n and m decrease in the same direction, the minus sign, if indices n and m increase in the same direction.

Assuming as before that M is an even integer, there are M values of $\Delta m$ in the range $-M/2+1, -M/2+2, \ldots, M/2-1, M/2$. Hence, for processing the measurement data acquired at a given source position $S_n$, one needs to look at the relative hitlist information $$I_{n \pm (-M/2+1)}, I_{n \pm (-M/2+2)}, \ldots, I_{n \pm (M/2-1)}, I_{n \pm (M/2)}$$

in order to know how that measurement data set contributes to the Radon positions in each of the φ-planes.

During runtime (imaging operation of the apparatus), the measured projection data (which may be pre-processed: normalized, scaled, corrected for detector non-uniformity's, etc.), is provided by DAS 17 to processor 18 for image reconstruction processing. As previously described, next one must perform many line integral calculations on the projection data in order to calculate the Radon data of the object.

In accordance with the principles of the present invention, speed-up of the Radon data calculations is achieved using an efficient parallel processing arrangement. The arrangement, shown in FIGS. 6–9, has the following features:

The number of discrete processors $N_p$ of the multiprocessor system is equal to the number of φ-planes in Radon space divided by an integer q. Thus, each processor handles one particular φ-plane (for the case where q=1), or a fixed set of q φ-planes.

The measurement data are broadcast to all the processors (i.e., the data are contained in a shared memory location to which all the processors have access). Each processor obtains and stores local copies of the measurement data to be used for the processing.

Each processor stores the hitlist information which it needs for its current task (processing the data from source $S_n$ for contribution to the fixed set of φ-planes) in its own, local memory.

The relative hitlist data (information $I_{n,m}$) are fed into the multiprocessor system in a pipeline fashion. After the data from source $S_n$ are processed, the hitlist information moves "downstream" such that every processor will have available in its associated local memory the information which is needed for processing the measurement data obtained at the next source position $S_{n+1}$.

Consider the processor responsible for the Radon $\phi_m$-plane and assume that indices n and m increase in the same direction. To process the data from source position $S_n$, this processor uses the hitlist information $I_{n+(M/2-m)}$. For the next source position $S_{n+1}$, the processor requires $I_{n+1+(M/2-m)} = I_{n+(M/2-(m-1))}$, the information which the processor responsible for the Radon $\phi_{m-1}$-plane (the "$\phi_{m-1}$-processor") uses to process the data from source position $S_n$. Hence, after the data from source position $S_n$ are processed, the "$\phi_{m-1}$-processor" needs to pass its current hitlist information on to the "$\phi_m$-processor", which, in turn, passes its current hitlist information on to the "$\phi_{m-1}$-processor", etc. On one end of the pipeline, the "$\phi_{M+1}$-processor" receives hitlist information, which is new (not yet used by another processor during the current reconstruction run), and the "$\phi_{M-1}$-processor" discards its current hitlist information because it will not be needed anymore for the subsequent source positions. The "feeding" of the pipeline can originate from any storage medium which holds the complete relative hitlist, e.g. from RAM ROM, disk, etc.

Figure 7:
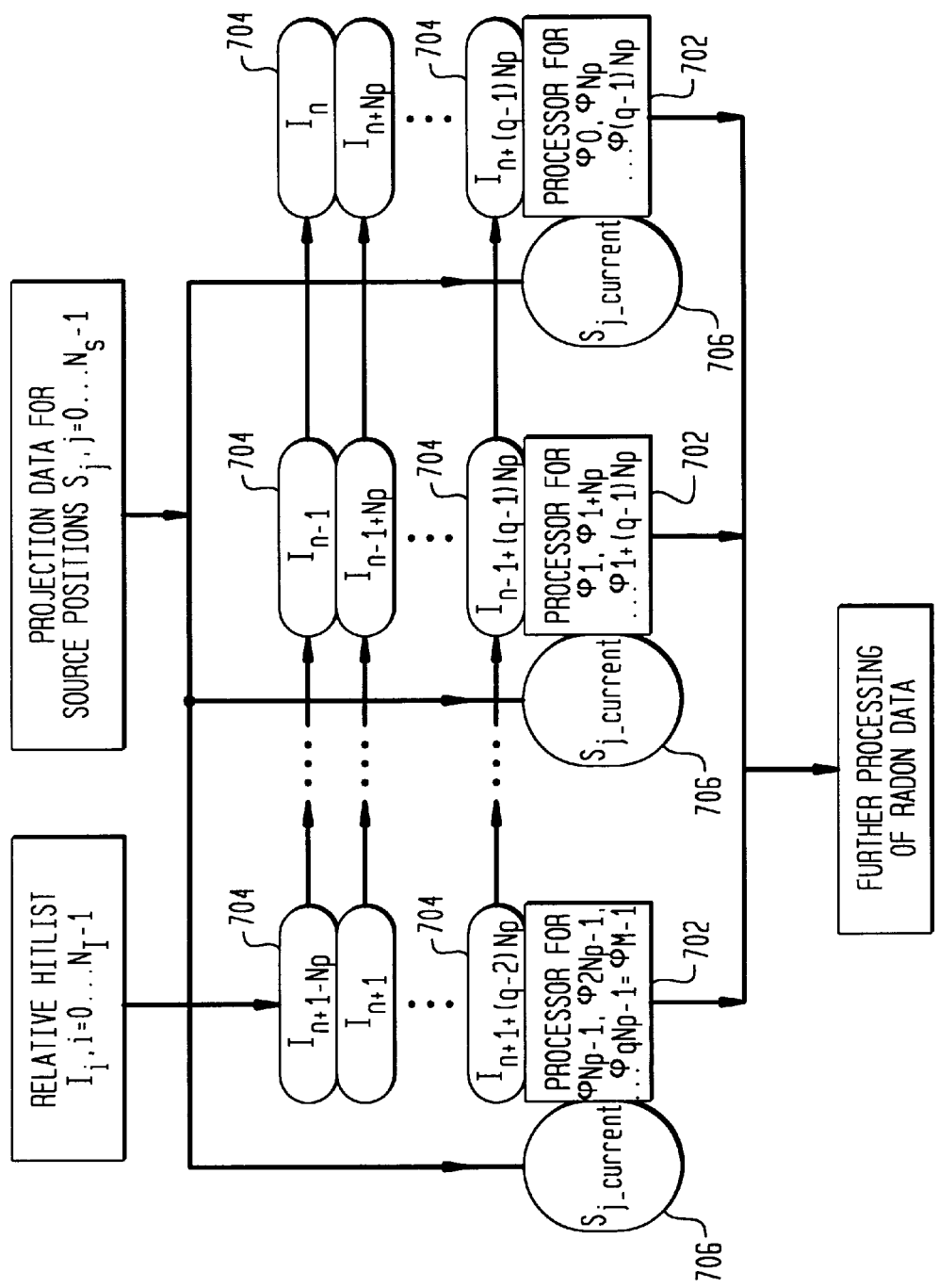
FIG. 7 illustrates an alternative embodiment for the inventive multiprocessor arrangement.

In the case where q>1, i.e., as shown in FIG. 7 where each processor is responsible for more than one $\phi$-plane, the $\phi$-planes are assigned to the processors in an interlaced fashion. Each processor works on every ($N_p$)th $\phi$-plane (instead of working on a block of q subsequent $\phi$-planes). This balances the load between the processors.

The processors are preferably specialized (i.e., contain specialized processing units) for the particular numerical task they have to perform, e.g. for line integration.

The Radon data calculated by the processors are accumulated and stored in local memory until they are calculated for all Radon positions. Further processing may occur at the same processors, on a $\phi$-plane by $\phi$-plane basis, or at another stage of processors. In the latter case, the data are either passed on to these other processors, or these other processors share the corresponding local memory of the previous processors.

Thus, the described architecture assigns different processors to different $\phi$-planes in Radon space. The measurement data are broadcast to local memories of the processors via a global broadcast bus. Hitlist data are propagated to (local memories of) the processors via local interconnects in a pipeline fashion. The calculated Radon data are stored in local memories of the processors until needed for further processing. The inventive arrangement not only keeps the amount of necessary data traffic low, but also handles it in an efficient manner.

Figure 6:
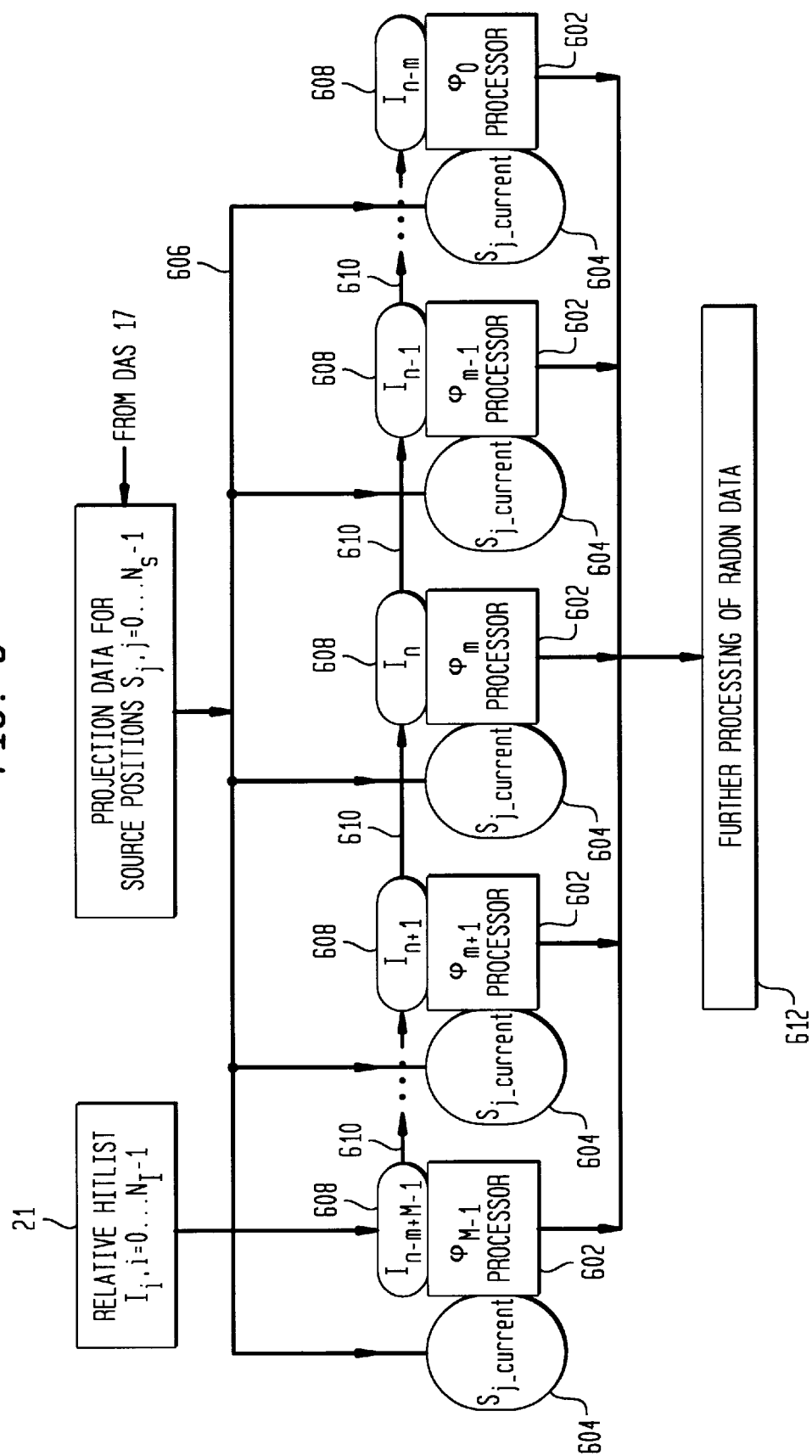
FIG. 6 illustrates a multiprocessor arrangement in accordance with the present invention for the processing of cone beam measurement data as shown in FIG. 1, to develop Radon derivative data.

More specifically, FIG. 6 illustrates one embodiment of an efficient multiprocessor implementation in accordance with the present invention. This arrangement assigns a different processor 602 to each Radon space $\phi$-plane. Measurement data ($S_j$) are broadcast to a respective one of a plurality of local memories 604 that are associated with a corresponding plurality of $\phi$-plane processors 602, via a global broadcast bus 606. Subsets of hitlist data ($I_j$, i=0 . . . $N_{I-1}$) are propagated from the central memory (database 21) to each of the $\phi$-plane processors 602 via a corresponding plurality of additional local memories 608. Local memories 608 are interconnected in a pipeline fashion via local interconnects 610. In response thereto, processors 602 calculate samples of Radon derivative data which are stored in further local memories (not shown) of $\phi$-plane processors 602 for further processing 612, so as to output the radial derivatives of the object's Radon transform, $\phi$-plane by $\phi$-plane. The illustrated multiprocessor arrangement could also perform the subsequent processing, i.e., integration of the Radon derivatives to yield the Radon transform, Radon inversion in the $\phi$-planes, and Radon inversion in the z-planes.

In operation each $\phi$-plane processor 602 obtains and stores local copies of the measurement data. Note, in an alternative embodiment local storage of the measurement data may not be desired.

A further local memory stores the hitlist information which is relevant for the current task of the processor (processing the data from source $S_n$ to develop contributions to the Radon data of a fixed set of $\phi$-planes). The relative hitlist data are fed by the further local memories to the multiprocessor system in a pipeline fashion. After the data from source $S_n$ are processed, the hitlist information moves "downstream" such that every $\phi$-plane processor 602 has now available in its local memory the information which is relevant for processing the measurement data from the next source position $S_{n+1}$. A start or initialization condition depends upon the specific boundary conditions of the scan path, and their calculation are well within the ability of one of ordinary skill in this technology.

Alternative embodiments

Case 1: where each of $N_p$ processors handles q different $\phi$-planes in an interlaced fashion, i.e., q>1.

An embodiment for this first alternative is illustrated in FIG. 7. Since each processor 702 is now responsible for q $\phi$-planes, each processor requires a corresponding number of q hitlist information "packets" $I_i$ for each set of projection data. Accordingly, the hitlist data are pipelined through the line of processors 702 in "bundles" of q information packets $I_i$ via local memories 704. The projection data are again broadcast to all the processors, one source position at a time, in the same manner as before and stored in local memories 706.

The illustrated index distribution assumes that n and m increase in the same direction. The current source index j_current for the depicted situation is j_current=n+M/2.

Case 2: where $\Delta\phi_{source} = k\Delta\phi_{Radon}$, where k is an integer.

Figure 8:
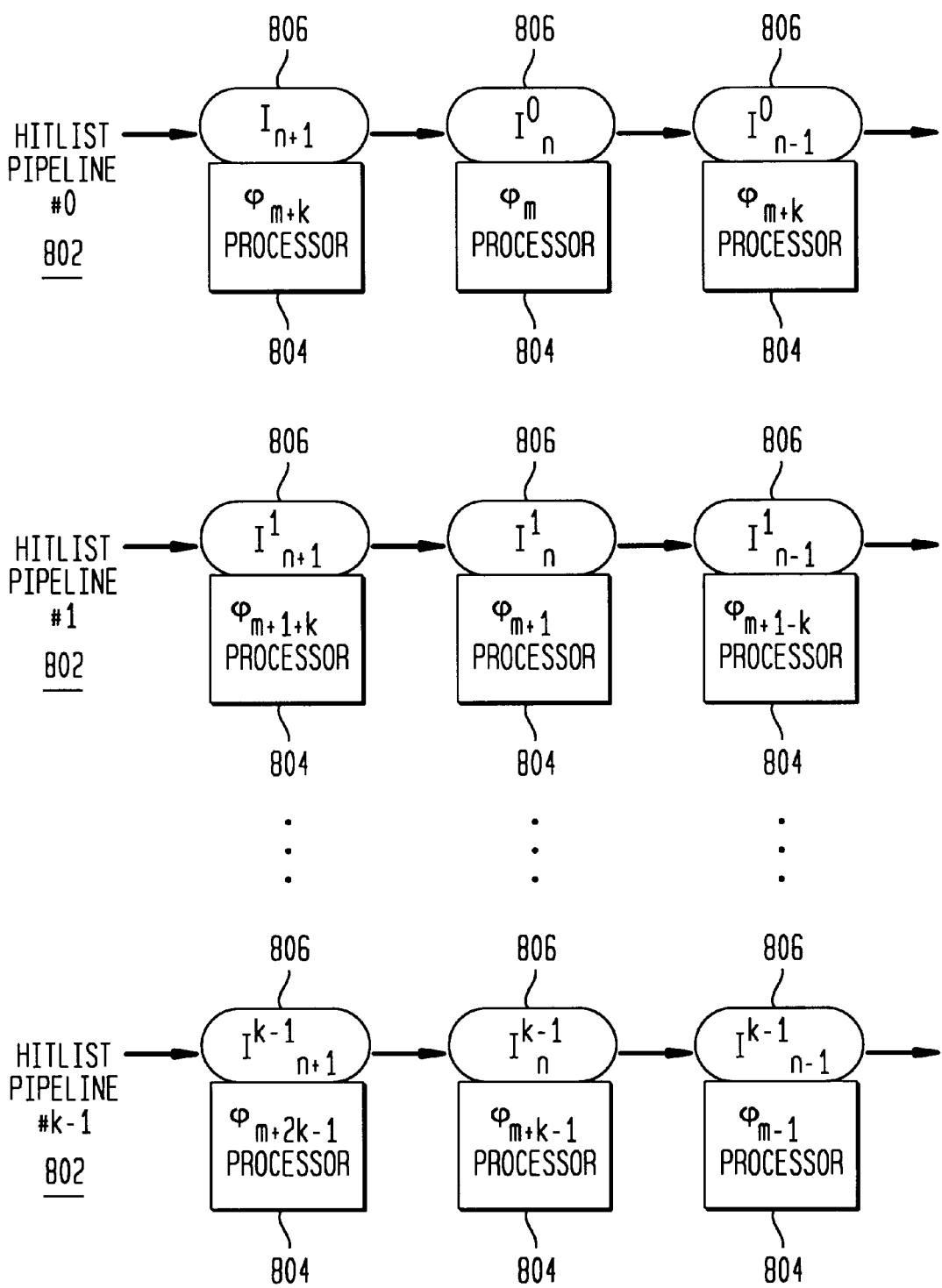
FIG. 8 illustrates a further alternative embodiment for the inventive multiprocessor arrangement.

In this alternative, shown in FIG. 8, the angular distance between the sampled source positions on the scan path is k-times larger than the angular distance of the $\phi$-planes in Radon space (commonly referred to as "source position undersampling"). This case can be accommodated by calculating k relative hitlists. The information stored in each relative hitlist pertains to the contribution of all the source positions to one of k subsets of $\phi$-planes. For the example where k=2, one relative hitlist would cover all $\phi$-planes with even indices, the other would cover the $\phi$-planes with odd indices.

Accordingly, this case is implemented by k separate pipelines 802 for feeding the hitlist information to the processors 804. Correspondingly, there are k sub-groups of processors which work on k separate sub-groups of the $\phi$-planes.

Source $S_n$ contributes to the $\phi_m$-plane according to
$I_{n,m} = I_{n\pm\Delta, M/2+t} \equiv I^t_{n\pm\Delta}$ with $\Delta$=floor($\frac{M/2-m}{k}$), t=m+k.$\Delta$−M/2,
with the same sign convention as before, i.e. the plus sign applies if indices n and m decrease in the same direction.

The relative hitlist (respectively the k relative hitlists) contain the information $I^t_n$ for n=0 . . . $N_s$−1, t=0 . . . k−1 which are pipelined to processors 804 via local memories 806.

Again, FIG. 8 shows only the distribution of the hitlist information, not the distribution of the measurement data. Each of the processors would hold the same set of measurement data at a given time.

Case 3: where $\Delta\phi_{Radon} = f\Delta\phi_{source}$, where f is an integer.

In this case, the angular distance between the $\phi$-planes in Radon space is f-times larger than the angular distance of the sampled source positions on the scan path ("source position oversampling"). This case requires a hitlist which can be composed by interlacing f relative hitlists, where each of these relative hitlists contains the information about a subset of source positions with respect to all the $\phi$-planes. For the example of f=2, one relative hitlist would cover all source positions with even indices, the other would cover the source positions with odd indices.

Figure 9A:
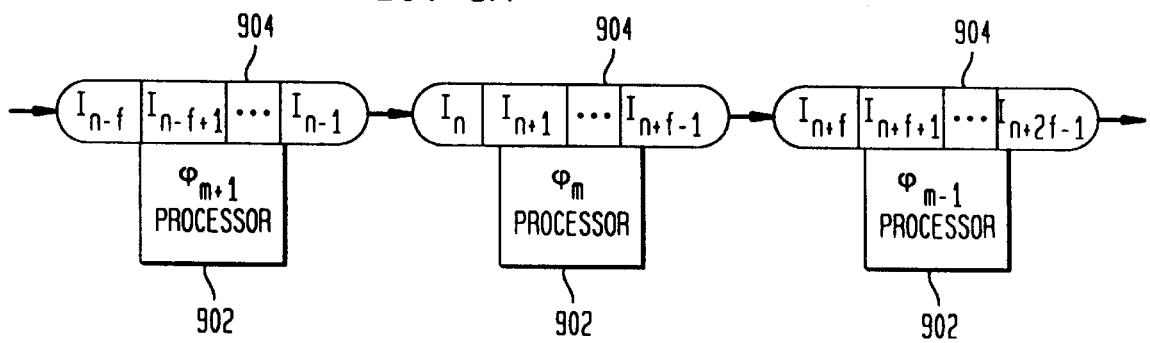
FIGS. 9a and 9b illustrate even further alternative embodiments for the inventive multiprocessor arrangement.
Figure 9B:
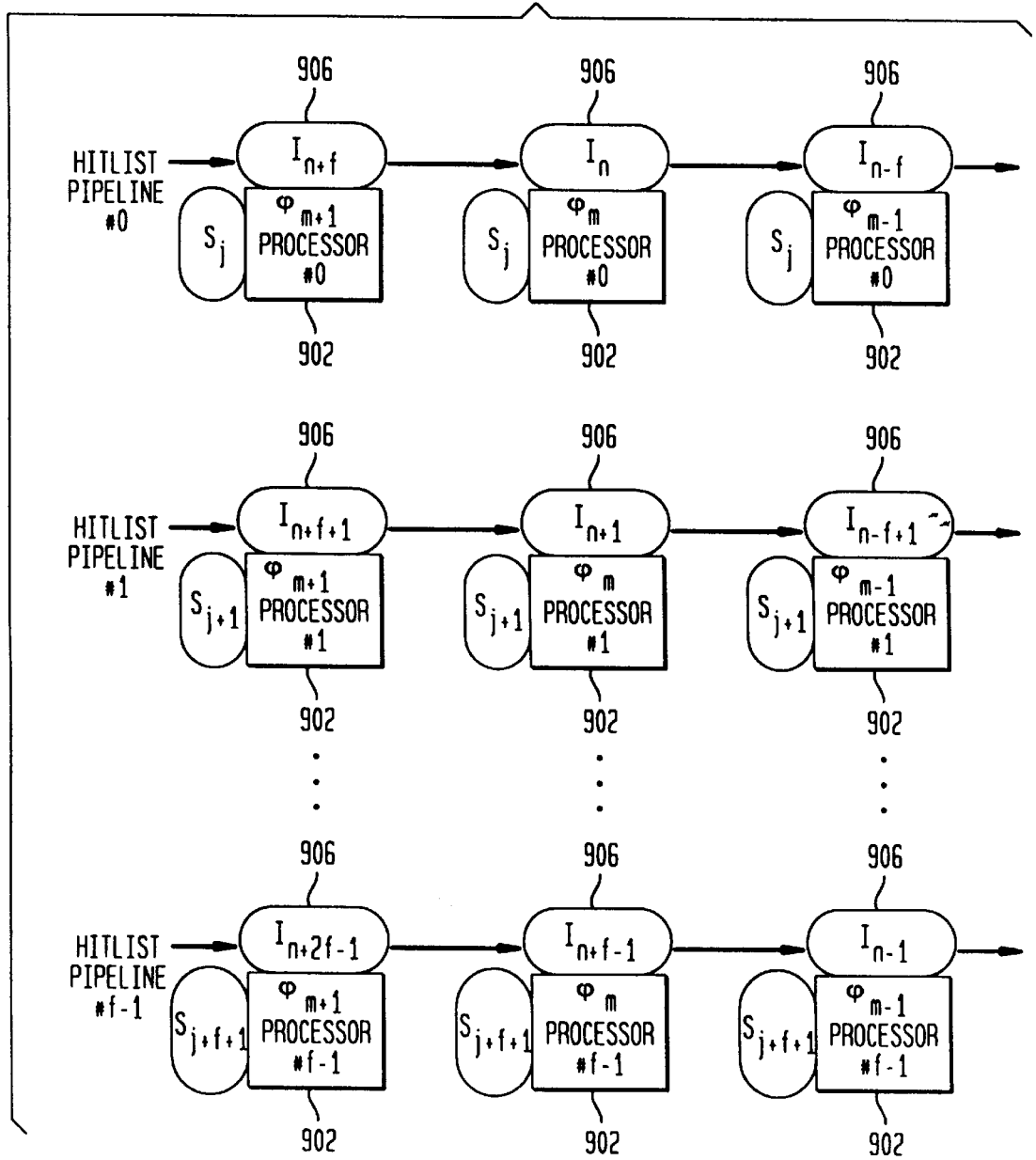

As shown in FIG. 9a, one can feed the large, single hitlist to the processors 902 in a single pipeline. Then, only an f-th part of the information stored at a local memory 904 associated with each processor 902 will be used to process the data from any given source position. Alternatively, as shown in FIG. 9b, one can have a different set of processors for each subset of source positions (i.e., if f=2: one set of processors handles source positions with even indices, and another set of processors handles the source positions with odd indices), to which one feeds to a respective one of memories 906 only the corresponding sub-hitlists. In this case, there would be now f processors working on each $\phi$-plane. Source $S_n$ contributes to the $\phi_m$-plane according to: $I_{n,m} = I_{n \pm f \cdot \Delta m, M/2} \equiv I_{n \pm f \cdot \Delta m}$ with $\Delta m = M/2 - m$, with the same sign convention before, i.e. the plus sign applies if indices n and m decrease in the same direction.

Thus, there has been shown and described a novel method and apparatus for greatly speeding-up and improving the efficiency of the image reconstruction processing in a cone beam 3D CT imaging apparatus. Many changes, modifications, variations and other uses and applications of the subject invention will, however, become apparent to those skilled in the art after considering this specification and its accompanying drawings, which disclose preferred embodiments thereof. For example, One can distribute the pre-calculated information to the processors not only in a pipeline fashion, i.e. by passing it along from local memory to local memory via local interconnects, the pre-calculated information may be stored in a central memory where it can be accessed by all the processors. Preferably, all the processors can access the memory in parallel. Such a parallel access can be implemented in the following way:

The memory is partitioned such that each "piece of memory" contains the information which is relevant for one processor to process one set of measurement data (respectively f sets of projection data for the case f>1). Each memory partition has its own interface through which it can be accessed.

The processors are connected to these interfaces via a non-blocking interconnect network, e.g. of crossbar type, such that at any given time each processor has access to the pre-calculated data it needs to perform its processing of the current measurement data.

The structure of the interconnection network may be simplified by taking into account that it need not provide arbitrary permutations between input and output channels. Rather, from one set of the measurement data to the next, the processors are switched to the memory partitions which their neighbor processors had been connected to before, i.e. the whole set of output channels just moves ahead by one input channel.

One can use the proposed parallel architecture to one's advantage not only when the structure of the pre-calculated information is as previously described. For example, the parallel architecture applies very well when one uses detector weight list information instead of hitlist information. U.S. patent application Ser. No. 08/994,605 FAST CONE BEAM IMAGE RECONSTRUCTION USING A DETECTOR WEIGHT LIST, filed Dec. 19, 1997 describes the construction and use of a detector weight list. For each bit of acquired measurement data (i.e. for each picture element of the 2-D detector array, at each measurement position of the detector-source assembly), weight factors which determine the contribution of this bit of pixel measurement data to samples of the radial derivative of the object's 3-D Radon transform, are pre-calculated and stored. These weight factors essentially represent the point-spread function between the detector space and 3-D Radon space. The pre-calculated pixel weights are organized by source position into what is referred to as a "detector weight list", with a subset of the weight list being provided for each source position. The pre-calculated weights of the detector weight list are stored in a database which are used during run-time operation of the apparatus for supplying weight factors which are multiplied with pre-processed measurement data acquired by the detector pixels at each source position so as to simply and quickly develop the Radon derivative data. When using a detector weight list approach for image reconstruction, there is no need to store copies of the measurement data in local memories of the processors because the projection data will be processed pixel by pixel, i.e. in a serial way. Thus, it is sufficient to "stream" the measurement data to the processors while the respective subsets of the detector weight list are individually passed in a pipeline fashion from one local memory to the next that are associated with respective ones of the parallel processors.

The basic principle is to have information "packets", each packet containing information about how the measurement data from one source position contributes to one $\phi$-plane in Radon space. These packets are distributed to the parallel processors (each processor being responsible for a fixed set of $\phi$-planes in Radon space) in a way that keeps data traffic low. Availability of these information packets allows a fast processing of the measurement data which are being broadcast to the parallel processors.

Depending on the nature of the pre-calculated information in these packets, the numerical task for the processors can vary, and different kinds of specialized processors, known to those familiar with this technology, may be appropriate for optimum performance. For processing the measurement data based on the hitlist information as described in the forenoted portion of the description entitled "Details of Hitlist Structure", the processors should contain specialized line integrators and adders. With regard to the alternative embodiment that processes detector weight list information, specialized multipliers and adders would be most efficient.

All such changes, modifications, variations and other uses and applications which do not depart from the general teaching of the invention herein, are deemed to be covered by this patent, which is limited only by the claims which follow as interpreted in light of the foregoing description.

What is claimed is:

1. A computed tomographic imaging apparatus for performing three-dimension (3D) image reconstruction of a region of interest (ROI) of an object, comprising:

scanning means including a cone beam radiation source and an area detector for scanning at a plurality of source positions about the ROI in the object for developing successive sets of cone beam measurement data representative of radiation attenuation caused by the ROI in the object, a central memory having stored therein a plurality of subsets of pre-calculated image processing information useful for converting the measurement data to Radon derivative data, and a plurality of processors, each of the processors having a first input coupled for receiving in a broadcast manner the successive sets of the measurement data, and a second input, responsive to a given sequence of successive ones of the subsets of pre-calculated image processing information for converting the measurement data to Radon derivative data on a plurality of Radon φ-planes.

2. The apparatus of claim 1, wherein said processors are coupled for receiving the subsets of pre-calculated image processing information in a sequence that causes said processors to convert the measurement data into Radon derivative data for a respective subset of said Radon φ-planes.

3. The apparatus of claim 1, further including a plurality of local memories coupled to one another for transferring the subsets of pre-calculated image processing information therebetween in a pipeline manner, an output of said local memories also being coupled to respective ones of said plurality of processors, so that a given subset of said pre-calculated image processing information is passed from one processor to a next one of the plurality of processors in synchronism with the broadcasting of the measurement data to said processors.

4. The apparatus of claim 1, wherein said given sequence corresponds with a sequence of said source positions used for scanning about the object.

5. A method for operating a computed tomographic imaging apparatus for performing three-dimensional (3D) image reconstruction of a region of interest (ROI) of an object, comprising the following steps:

operating a cone beam radiation source and an area detector for scanning at a plurality of source positions about the ROI in the object, so as to develop successive sets of cone beam measurement data representative of radiation attenuation caused by the ROI in the object, providing a central memory having a plurality of subsets of pre-calculated image processing information useful for converting the measurement data to Radon derivative data, and processing the measurement data for converting it to Radon derivative data on a plurality of Radon φ-planes, said processing comprising broadcasting the successive sets of measurement data to a plurality of processors, simultaneously with application to said processors of a given sequence of successive ones of the subsets of pre-calculated image processing information.

6. The method of claim 5, wherein the subsets of pre-calculated image processing information are applied to said processors in a pipeline manner using a plurality of local memories, so that a given subset of said pre-calculated image processing information is passed from one processor to a next one of said plurality of processors in synchronism with the broadcasting of the measurement data to said processors.

7. The method of claim 5, wherein said given sequence corresponds with a sequence of said source positions used for scanning about the object.

* * * * *